US00PP35340P2

(12) United States Plant Patent
Danziger

(10) Patent No.: US PP35,340 P2
(45) Date of Patent: Aug. 22, 2023

(54) ***IMPATIENS* PLANT NAMED 'DIMPSLNRD'**

(50) Latin Name: *Impatiens hawkeri*
Varietal Denomination: DIMPSLNRD

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 18/075,249

(22) Filed: Dec. 5, 2022

(51) Int. Cl.
*A01H 5/02* (2018.01)
*A01H 6/16* (2018.01)

(52) U.S. Cl.
USPC ..... Plt./318.7
CPC ..... *A01H 6/165* (2018.05)

(58) Field of Classification Search
USPC ..... Plt./318.7
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Impatiens* plant named 'DIMPSLNRD' is disclosed, characterized by large, red flowers and dark green foliage. Plants are compact, mounded, and sun-resistant. The new variety is an *Impatiens*, typically produced as an ornamental plant.

2 Drawing Sheets

Figure 1:
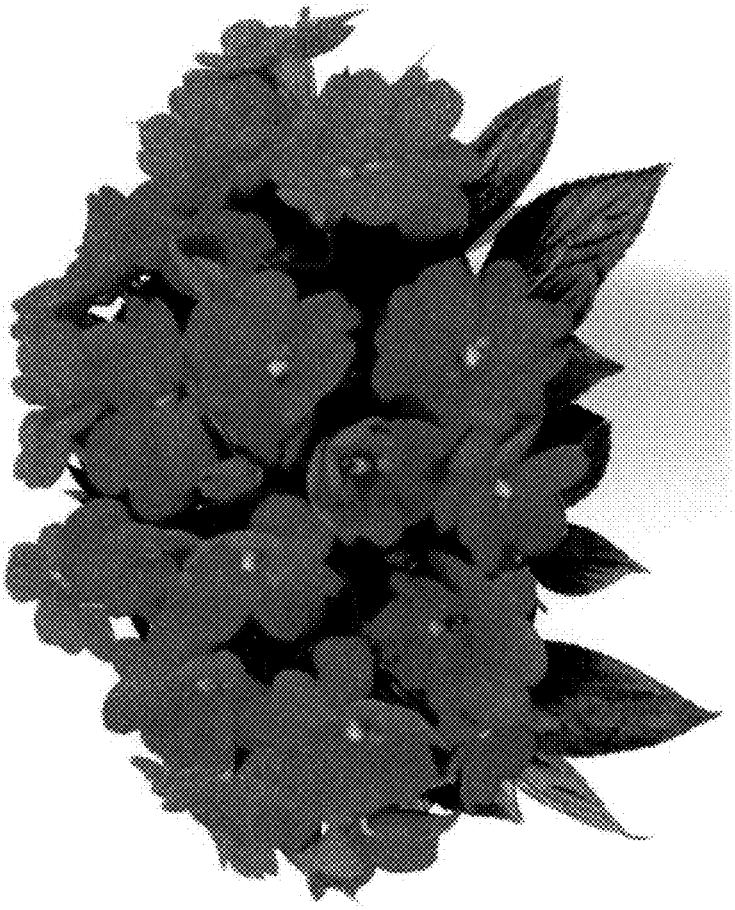

Latin name of the genus and species: *Impatiens hawkeri.*
Variety denomination: 'DIMPSLNRD'.

BACKGROUND OF THE INVENTION

The new *Impatiens* cultivar is a product of a planned breeding program conducted by the inventor, Gavriel Danziger in Moshav Mishmar Hashiva, Israel. The objective of the breeding program was to produce useful new *Impatiens* varieties for ornamental horticultural production. The crossing resulting in this new variety was made during July of 2018.

The seed parent is the unpatented, propriety variety referred to as *Impatiens* 'BM-16-1296'. The pollen parent is the unpatented, propriety variety referred to as *Impatiens* 'BM-16-1345'. The new variety was discovered in May of 2019 by the inventor in a group of seedlings resulting from the 2018 crossing, in a greenhouse in Moshav Mishmar Hashiva, Israel. After selection of the new variety, extensive confidential testing has been performed to determine and define the desirable characteristics of the new variety.

Asexual propagation of *Impatiens* was performed by leaf cuttings in May of 2019, at the same nursery in Moshav Mishmar Hashiva, Israel and has shown that the unique features of this cultivar are stable and reproduced true to type in multiple successive generations. Date of first sale is Jan. 2, 2022, in the United States. This sale was made directly by the inventor or one who obtained the claimed invention directly or indirectly from the inventor. This sale and all public disclosures made between Jan. 2, 2022, and the filing of this application fall within the exception allowed under 102(b)(1).

SUMMARY OF THE INVENTION

The cultivar 'DIMPSLNRD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DIMPSLNRD'. These characteristics in combination distinguish 'DIMPSLNRD' as a new and distinct *Impatiens* cultivar:

1. Large, red flowers.
2. Dark green leaves.
3. Sun-resistant.

PARENT COMPARISONS

Plants of 'DIMPSLNRD' are similar in some horticultural characteristics to the seed parent. The new variety, however, differs in the following:

1. Flowers of the new variety are red, while flowers of the seed parent are pink.
2. Flowers of the new variety are larger than flowers of the seed parent.

Plants of 'DIMPSLNRD' are similar in some horticultural characteristics to the pollen parent. The new variety, however, differs in the following:

1. Flowers of the new variety are red, while flowers of the pollen parent are dark pink.
2. Leaves of the new variety are darker green than leaves of the pollen parent.

COMMERCIAL COMPARISONS

Plants of 'DIMPSLNRD' are similar in some horticultural characteristics to the variety *Impatiens* 'Sun Harmony Red', unpatented. The new variety, however, differs in the following:

1. Growth habit of the new variety is more compact than the growth habit of this comparator.
2. Leaves of the new variety are darker green than leaves of this comparator.

3. Flower color of the new variety is darker than flower color of this comparator.

Plants of 'DIMPSLNRD' are similar in some horticultural characteristics to the variety *Impatiens* 'DHARSSCRLTR', U.S. Plant Pat. No. 27,263. The new variety, however, differs in the following:

1. Leaves of the new variety are darker green than leaves of this comparator.
2. Flowers of the new variety are smaller than flowers of this comparator.
3. Leaves of the new variety are smaller than leaves of this comparator.

BRIEF DESCRIPTION OF THE PHOTOGRAPHS

The accompanying photograph in FIG. 1 illustrates in full color a typical plant of 'DIMPSLNRD' at about 4 weeks of age, grown in a 12 cm pot.

Figure 2:
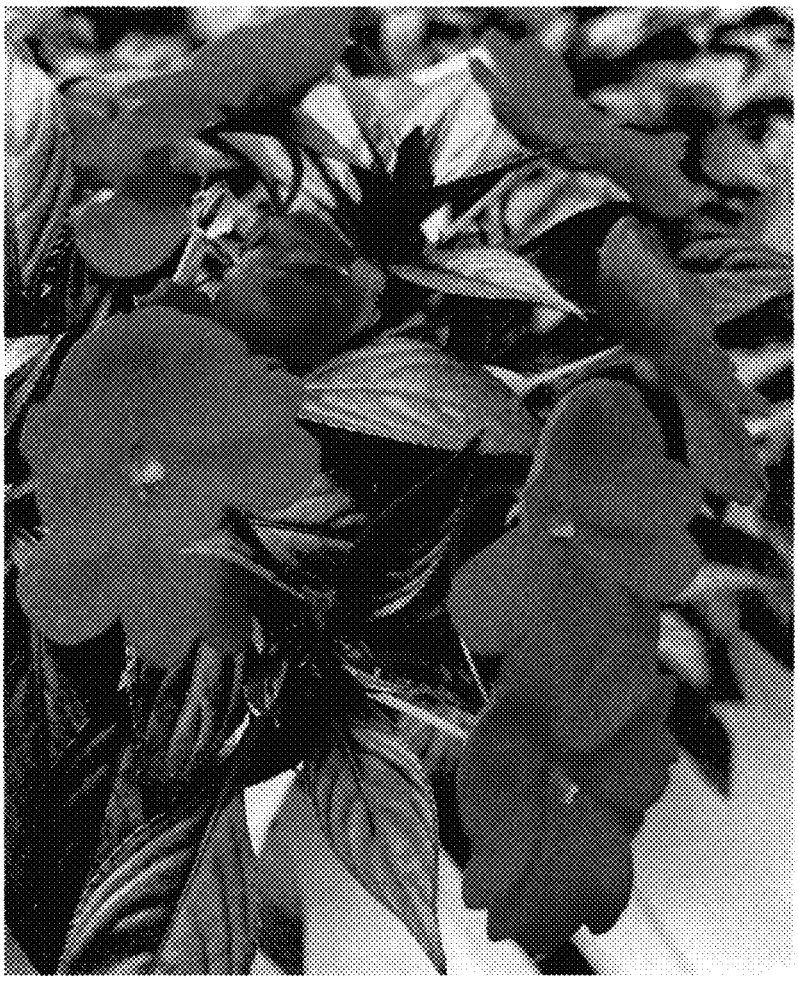

FIG. 2 illustrates a close-up view of typical flowers and foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DIMPSLNRD' plants grown in a greenhouse in Moshav Mishmar Hashiva, Israel, under natural lighting. Measurements were taken during autumn. The growing temperature ranged from approximately 20° C. to 30° C. during the days, 15° C. to 25° C. during the nights. Measurements and numerical values represent averages of typical plant types.

Botanical classification: *Impatiens hawkeri* 'DIMPSLNRD'.

PROPAGATION

Time to initiate rooting: 10 to 14 days in summer; 14 to 20 days in winter.

Age of plant described: 12 weeks from a rooted cutting.

Root description: Fibrous, adventitious.

PLANT

Growth habit: Compact, mounded.

Pot size of plant described: 13 cm.

Height: 20 to 25 cm.

Plant spread: 30 to 35 cm.

Growth rate: Medium.

Branching characteristics: Medium branched.

Length of primary lateral branches: 18 to 20 cm.

Quantity of primary lateral branches: 5 to 10.

Characteristics of primary lateral branches:

*Shape.*—Oval.
*Diameter.*—0.5 cm.
*Texture.*—Smooth.
*Strength.*—Strong, very stable.
*Color.*—RHS Greyed-Orange 176B.

Internode length: 4 to 8 cm.

FOLIAGE

Leaf:

*Arrangement.*—Alternate.
*Quantity.*—Approximately 15 to 20 per branch.
*Average length.*—8 cm.
*Average width.*—3.5 cm.
*Pubescence.*—None.
*Shape.*—Lanceolate.
*Apex.*—Apiculate.
*Base.*—Acuminate.
*Margin.*—Ciliate.
*Texture.*—Smooth.
*Aspect.* 45°.
*Color.*—Young Foliage, Upper Side: Near RHS Green 137B. Young Foliage, Under Side: Near RHS Greyed-Green 195A. Mature Foliage, Upper Side: Near RHS Yellow-Green 147A. Mature Foliage, Under Side: Near RHS Greyed-Green 195A.
*Venation.*—Type: Pinnate. Color, Upper Side: RHS Greyed-Red 182C. Color, Under Side: RHS Greyed-Red 182A.

Petiole:

*Length.*—1 cm.
*Diameter.*—0.2 cm.
*Color.*—RHS Greyed-Purple 185D.
*Texture.*—Smooth.

FLOWER

Natural flowering season: Year-round in a greenhouse environment. Flowering is continuous from spring to autumn outdoors.

Days to flowering from rooted cutting: 10 weeks.

Inflorescence and flower type and habit: Single flowers raised above the foliage. Corolla consists of 5 petals.

Rate of flower opening: 5 to 15 days from bud to fully opened flower.

Flower longevity on plant: 5 to 8 days.

Persistent or self-cleaning: Self-cleaning.

Bud:

*Shape.*—Ovate.
*Length.*—2 cm.
*Diameter.*—1 cm.
*Color.*—RHS Red 46B.

Flower size:

*Diameter. About* 7 cm.
*Depth.*—About 4 cm.

Corolla/petals:

*Arrangement.*—Overlapping.
*Length.*—3.5 cm.
*Width.*—3.5 cm.
*Quantity.*—5.
*Texture.*—Smooth, upper and lower.
*Apex.*—Heart-shaped.
*Shape.*—Obcordate.
*Margin.*—Entire.
*Color.*—When Opening, Upper Surface: RHS Red 45B. When Opening, Lower Surface: RHS Red 43A. Fully Opened, Upper Surface: RHS Red 45B. Fully Opened, Lower Surface: RHS Red 44B.

Spurs:

*Quantity.*—1 per flower.
*Length.*—7 to 7.5 cm.

*Diameter.*—0.1 cm.
*Aspect.*—Spur curvature 40° to 45° from peduncle.
*Color.*—RHS Red 51A towards base; Green 142B at apex.

Sepals:
*Quantity.*—2 per flower.
*Shape.*—Oblong.
*Length.*—1 cm.
*Width.*—0.5 cm.
*Apex.*—Caudate.
*Base.*—Rounded.
*Margin.*—Entire.
*Color.*—RHS Greyed-Green 193B.

Peduncles:
*Length.*—6.5 cm.
*Width.*—0.2 cm.
*Angle.*—About 45° to lateral branch.
*Strength.*—Stable, flexible.
*Texture.*—Smooth.
*Color.*—RHS Green 138D.

Fragrance: None.

REPRODUCTIVE ORGANS

Androecium:
Stamens:
*Quantity.*—5, with anthers that are more or less fused, forming a cap over the ovary.

Anthers:
*Shape.*—Oblong.
*Length.*—About 0.5 cm.
*Color.*—RHS White 155B.
*Pollen.*—Color: RHS White NN155A. Amount: Medium.

Gynoecium:
Pistil:
*Quantity.*—1.
*Length.*—0.5 cm.
*Style.*—Length: 0.5 cm. Color: RHS Yellow-Green 144B.
*Stigma.*—Shape: Round. Color: RHS Yellow-Green 144D. Ovary Color: RHS Yellow-Green 144D.

OTHER CHARACTERISTICS

Seeds and fruits: Not observed.
Disease/pest resistance: Neither resistance nor susceptibility of diseases and pests common to *Impatiens* observed.
Temperature tolerance: Tolerant of temperatures between 5° C. and 30° C. Grows best at 10° C. to 28° C.

What is claimed is:

1. A new and distinct cultivar of *Impatiens* plant named 'DIMPSLNRD' as herein illustrated and described.

* * * * *